(12) United States Patent
Kraus et al.

(10) Patent No.: US 6,712,846 B1
(45) Date of Patent: *Mar. 30, 2004

(54) POLYMER-COATED STENTS, PROCESSES FOR PRODUCING THE SAME AND THEIR USE FOR RESTENOSIS PREVENTION

(75) Inventors: Werner Kraus, Berlin (DE); Hartwig Hocker, Aachen (DE); Jorg Lahann, Aachen (DE); Doris Klee, Aachen (DE)

(73) Assignees: Schering Aktiengesellschaft, Berlin (DE); Angiomed GmbH & Co. Medizintechnik KG, Karlsruhe (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/403,923
(22) PCT Filed: Apr. 29, 1998
(86) PCT No.: PCT/EP98/02528
§ 371 (c)(1), (2), (4) Date: Jun. 5, 2000
(87) PCT Pub. No.: WO98/48852
PCT Pub. Date: Nov. 5, 1998

(30) Foreign Application Priority Data

Apr. 30, 1997 (DE) .......................................... 197 18 339

(51) Int. Cl.[7] .................................................. A61F 2/06
(52) U.S. Cl. ........................ 623/1.46; 623/1.1; 623/1.42
(58) Field of Search ........................ 623/1.1, 1.41–1.43, 623/1.46–1.48, 1.11; 600/3; 604/103.02; 514/772.2, 449

(56) References Cited

U.S. PATENT DOCUMENTS

| 5,053,048 A | * | 10/1991 | Pinchuk ........................ 623/1.1 |
| 5,059,166 A | * | 10/1991 | Fischell et al. ................. 600/3 |
| 5,609,629 A | * | 3/1997 | Fearnot et al. ................ 623/1.1 |
| 5,797,887 A | * | 8/1998 | Rosen et al. ................. 623/1.42 |
| 5,877,224 A | * | 3/1999 | Brocchini et al. ........ 614/772.2 |
| 5,893,840 A | * | 4/1999 | Hull et al. .............. 604/103.02 |
| 5,977,163 A | * | 11/1999 | Li et al. ....................... 514/449 |
| 6,146,358 A | * | 11/2000 | Rowe ......................... 623/1.11 |

FOREIGN PATENT DOCUMENTS

| DE | 43 15 002 C | 8/1994 |
| EP | 0 433 011 A | 6/1991 |
| EP | 0 819 446 A | 1/1998 |
| WO | WO 97/38730 A | 10/1997 |

* cited by examiner

Primary Examiner—Julian W. Woo
(74) Attorney, Agent, or Firm—Millen, White, Zelano & Branigan, P.C.

(57) ABSTRACT

The invention relates to polymer-coated stents, processes for their production and their use for restenosis prevention.

33 Claims, No Drawings

POLYMER-COATED STENTS, PROCESSES FOR PRODUCING THE SAME AND THEIR USE FOR RESTENOSIS PREVENTION

The invention relates to stents with polymer coating, processes for their production and their use for preventing restenosis.

THE PRIOR ART

Stents are prior art (Pschyrembel, Klinisches Wörterbuch [Clinical Dictionary], 257$^{th}$ edition, W. de Gruyter Publisher). Stents are endoprostheses that make it possible to keep duct-like structures open in the bodies of humans or animals (e.g., vessel, esophageal, tracheal, bile duct stent). They are used as palliative measures for constrictions by closure (e.g., atherosclerosis) or by external pressure (e.g., from tumors). Radioactive stents are used for restenosis prevention, for example, after surgical intervention in the vessels or interventional radiological procedures (e.g., balloon angioplasty).

The surface of the previously described stents is either metallic and consists, e.g., of stainless steel, nitinol or gold, or is covered with a layer of a polymer, e.g., with polyurethane, polylactic acid, polyglycolic acid or copolymers.

Stents are also known that are coated with a polymer layer that contains a therapeutic agent and gradually releases it. Such a stent is described, e.g., in patent application WO 91/12779.

In European patent application EP 0 819 446 A2, a stent coated with a chelating agent is described. The stent is dipped in a solution with a radioisotope before implantation, so that a radioactive implant is achieved. But in contrast to other therapeutic agents, the radioisotope is not to reach the blood stream. But in the stents proposed in this application, the selected chelating agents all have poor properties as complexing agents, so that it is not guaranteed that the radioisotope remains bonded to the stent.

Now the problem exists that the stent, for the body, is a foreign object and intolerance reactions occur. Further, it must be guaranteed for a radioactive implant that the radioactive isotope is permanently bonded to the surface and will not come off in vivo.

The object of this invention is thus to make available stents that are tolerated better than conventional stents and to whose surface therapeutic agents are bonded. If radioisotopes are used as therapeutic agents, then the radioactive isotopes must be permanently bonded to the stent surface so that the radioactive ions do not come off in vivo.

This object is achieved by the stents described below as they are characterized in the claims.

DESCRIPTION OF THE INVENTION

The object outlined above is achieved according to the invention in that the surface of the stent is coated with a polymer to which hydrophilic substances are coupled that additionally can represent or contain a therapeutic agent.

The device according to the invention thus consists of a base stent element to which a polymer is applied that carries hydrophilic substances having a particular affinity for therapeutic agents.

Commercially available implants can be used as base elements, e.g., a nitinol, stainless steel or gold stent. The Memotherm® stent, Wiktor stent, Strecker Stent or Palmaz-Schatz stent are common. Nitinol stents are preferably used.

Modified polyurethanes to whose surface hydrophilic substances are coupled, e.g., polyethylene glycols, polysaccharides, cyclodextrins or polyaminopolycarboxylic acids can be considered as polymers.

The therapeutic agents form either complexes with the hydrophilic substances (e.g., radioactive metal ions form very stable metal complexes with DTPA) or inclusion compounds (e.g., cyclodextrin forms a very stable inclusion compound with Iloprost).

To the extent that the hydrophilic substances have complexing properties, they can fix metal ions or radioactive isotopes. Polyaminopolycarboxylic acids, crown ethers, bis-oligo- or polyphosphonates, oligo- or polypeptides, sugar such as chitosan or cyclodextrin derivatives are examples of complexing chelating agents.

Polyaminopolycarboxylic acids in the context of this document are, e.g., DTPA, DOTA, DO3A, TTHA and their derivatives. Let us also mention, as examples, the compounds BOPTA, butylphenyl-DTPA, DTPA-BMEA, DTPA-BMA, dicyclohexyl-DTPA, dicyclohexyl-DOTA, DPDP, DTPA- or DOTA-substituted polymers, GlyMeDOTA such as GlyMeDOTA-substituted polymers and porphyrin derivatives.

The radioactive isotopes of the elements Ag, Au, Ba, Bi, C, Co, Cr, Cu, Fe, Ga, Gd, Hg, Ho, In, Ir, Lu, Mn, P, Pb, Pd, Pm, Re, Rh, Ru, Sb, Sc, Sm, Tb, Tc or Y can be used as radioactive isotopes.

The stents according to the invention can be produced, for example, as follows:

1. With Stents Coated with Radiotherapeutic Agents 1.1 An uncoated stent can first be coated with a polymer (e.g., a polyurethane, obtainable from the reaction of an amphiphilic polyether, diphenylmethane-4,4'-diisocyanate and butanediol). This polymer is modified so that it carries complexing agents (e.g., DTPA groups) on the surface. The polymer is dissolved in a solvent (e.g., chloroform) and the stent is dipped in the polymer solution. After removal of the stent from the polymer solution, it is dried in a drying chamber at room temperature. The hydrophilic stent is ready for use.

1.2 The stent coated according to 1.1 is treated with a solution of radioactive metal (e.g., $^{111}InCl_3$, $^{90}Y$). After washing the stent, this stent, coated radiotherapeutically, is ready for use.

1.3 In a variant of this process, the stent is coated in two stages. For this purpose, first the stent is treated with a polymer containing amino groups. The amino groups are present optionally in protected form during the polymerization. Then the amino groups are reacted with DTPA-monoanhydride, as it is described in the literature. The stent now has a polymer coating containing complexing agents (here: DTPA). The stent coated this way is then treated with a solution of radioactive metal (e.g., $^{111}InCl_3$, $^{90}Y$). After washing the stent, it is ready for use.

1.3. In another variant of the process, the stent coated with the bonding agent (polymer containing complexing agents) is implanted in an organism. A solution of a radioactive isotope is then administered intravascularly. In this process, the stent is coated radioactively in vivo. In this variant, the complexing agent portion of the bonding agent can be coated with physiologically tolerated metals (e.g., sodium, calcium, zinc, potassium, lithium, magnesium) to increase the tolerance of the implant. Thus, e.g., calcium ions can be complexed by the DTPA groups.

2. Stents Coated with Nonradioactive Therapeutic Agents 2.1 An uncoated stent can first be coated with a polymer (e.g., a polyurethane, obtainable from the reaction of an amphiphilic polyether, diphenylmethane-4,4'-diisocyanate and butanediol). This polymer is modified so that is has cyclodextrin on the surface. The polymer is dissolved in a solvent (e.g., chloroform) and the stent is dipped in the polymer solution. After removing the stent from the polymer solution, it is dried in a drying chamber at room temperature. The hydrophilic stent is ready for use.

2.2 The stent coated according to 2.1 is treated with a solution of the therapeutic agent (e.g., Iloprost). The therapeutic agent forms an inclusion compound with the cyclodextrin and stays bonded to the stent. After washing, the therapeutically coated stent is ready for use. The above-described processes are generally performed at temperatures of 0–80° C. Suitable solvents can be used for coating the stent depending on the respective polymer. When a nonaqueous solvent is used, it should be removed before implantation.

The radioactive stents can also be coated with two or more different isotopes. In particular it is possible to apply short- and long-lived isotopes together on one stent (e.g., $^{55}$Co with $^{55}$Fe or $^{99}$Mo with $^{57}$Co).

The work steps necessary to perform the processes described in principle above are known to one skilled in the art. Particular embodiments are described in detail in the examples.

Another process for the production of polymer-coated, radioactive stents is based on the process disclosed in German laid-open specification DE 196 04 173 A1, a process for creating antithrombogenic surfaces on medical objects. In this process, a functionalized polymer is applied to the base metal element of the stent by chemical vapor deposition at increased temperatures and reduced pressures. If a polymer containing an amino group is applied, then the stent can be treated after the polymer coating with a solution that contains a complexing agent in reactive form, e.g., DTPA-anhydride. A chemical reaction causes a true bonding, e.g., covalent bonding, between the polymer and the complexing agent. Alternatively, the polymer-coated stent can also be treated with spacer molecules such as, e.g., diisocyanates or dicarboxylic acid chlorides to which, in another reaction step, the complexing agent is bonded. A spacer molecule in the context of this application is a molecule that is suited for a chemical joining between the polymer surface and the complexing agent and provides the effect of a spacer.

The complexing agents used are, e.g., DTPA, DOTA, DO3A, and TTHA, which all have especially good complexing properties. They form especially stable complexes with metal ions so that, after dipping a stent coated with polymer and complexing agents in a solution with radioactive metal ions, these ions remain bonded to the surface of the stent. The stability of the metal complex is so good that the metal ions do not come off the implant even in vivo. Preferred isotopes are $^{186}$Re, $^{188}$Re, $^{111}$In, $^{90}$Y, $^{55}$Co, $^{57}$Co, $^{55}$Fe and $^{99}$Mo. It is also possible in this embodiment to apply several radioisotopes simultaneously to the stent. The radioisotopes can emit β or γ radiation.

Further, the radioactive stents according to the invention can also be produced by applying the polymer layer, with the help of plasma polymerization of olefins, to the base stent element. This process is described, e.g., in German laid-open specification DE 196 47 280 A1. Suitable olefins are, e.g., allylamine, allylalcohol, propargyl alcohol, butenols, butylamines, acrylic acid, acrylic acid derivatives, acrylates and hydroxymethyl acrylate. Complexing agents can be bonded either directly or by a spacer molecule to the functional groups of the polymer layer produced this way. The stents produced this way also are preferably treated before implantation with solutions containing radioactive metal ions of the isotopes $^{186}$Re, $^{188}$Re, $^{111}$In, $^{90}$Y, $^{55}$Co, $^{57}$Co, $^{55}$Fe and $^{99}$Mo.

It is also possible to apply to the stent, in addition to the radioactive substances, medicines such as Iloprost. Prostaglandin derivatives such as Iloprost can be inserted, as described above, in cyclodextrin derivatives located on the modified polymer surface.

The stents according to the invention achieve the above-described object. The stents according to the invention are well tolerated physiologically.

Stents containing complexing agents can be tagged radioactively with exact dosing by the disclosed processes without problems. As was able to be shown in the animal model, restenosis after balloon denudation was significantly inhibited by implantation of the radioactive stent according to the invention.

The particular advantage of the stent according to the invention is that the medical practitioner can select a stent according to his needs in advance and then activate the selected stent by the described process. The activation is performed by adding one or more radioactive isotopes and/or by applying one or more medicines that are inserted in the carrier (chelating agent or cyclodextrin). This makes it possible to adjust to the individual needs of the respective patient. The few materials and solutions needed for it can be delivered suitably prepared so that the medical practitioner in question need only dip the still uncoated stent in the predetermined sequence in the individual solutions. The invention thus relates also to materials, solutions, and preparations (kits) prepared for the process according to the invention.

Another advantage of the radioactive stent according to the invention is that, because of the especially good complexing properties of the selected chelating agents, the radioisotopes are so permanently bonded to the polymer surface that they do not come off the stent surface in vivo and/or are not exchanged for other ions. The tolerance of the radioactive stent according to the invention is considerably increased in comparison to the known radioactive stents.

EXAMPLES

The following examples are to explain the object of the invention in a nonlimiting way.

Example 1

$^{188}$Re-DTPA-loaded Stent

Polyurethane, obtainable by reacting an amphiphilic polyether, diphenylmethane-4,4'-diisocyanate and butanediol as a chain lengthener, is used as the polymer. To increase the yield of groups able to couple, additional functions, such as e.g., amino groups, can be contained in the individual components and they can optionally be present in protected form during the polymerization. The stents are coated by dipping them in a 5% chloroform solution of the polymer. Afterward, they are left to dry in a clean-room drying chamber at room temperature. The average layer thickness is 20 μm. The coating with the DTPA ligands is performed by reacting free amino groups with DTPA monoanhydride, as it is described in the literature and is known to one skilled in the art. The complexing is performed, also as is known to one skilled in the art, with a solution of a rhemium salt. Then the stent is ready for use.

Example 2
$^{111}$In-DTPA Stent Kit

The coating of the stent with the polymer and the subsequent reaction with DTPA monoanhydride are performed as described in example 1. The stent is now delivered in this form to the radiologist. Shortly before administration, the radiologist dips the stent in a solution with $^{111}$In ions, to activate it this way. Then the stent is implanted.

Example 3
$^{111}$In-DTPA Stent Kit

The coating of the stent with the polymer is performed as described in example 1. The stent is now delivered in this form to the radiologist. Shortly before administration, the radiologist dips the stent in a solution of DTPA monoanhydride, to apply the ligands to the stent. After taking the stent out of the solution and drying it, the subsequent reaction with $^{111}$In ions is performed. For this purpose, the stent is dipped in a second solution containing $^{111}$In ions, to activate it this way. After drying it again, the stent is implanted.

Example 4
$^{111}$In-DTPA Stent Kit

The coating of the stent with the polymer and the subsequent reaction with DTPA monoanhydride are performed as described in example 1. The stent is now delivered in this form to the radiologist. After administration of the stent, the radiologist injects a solution with radioactive $^{111}$In ions through the application catheter. This solution flows by the implanted stent and the radioisotopes are selectively removed from the solution by the ligands bonded to the stent and are fixed permanently on the stent.

Example 5

The coating of a metal stent by chemical vapor deposition (CVD) polymerization of 4-amino-[2,2]-paracyclophane is performed in a suitably designed unit. The unit is connected to an argon pressure cylinder, since argon functions as the carrier gas. The argon feed is with a 380 mm-long quartz glass tube with an outer diameter of 30 mm. The quartz glass tube is connected on its other end to a stainless steel pressure container. The quartz glass tube is supported floating freely in a three-zone tube furnace with a heated length of 320 mm and an inner diameter of 32 mm. All three heating zones can be heated to 800° C.

The stent to be coated is fixed by the removable viewing glass to the sample container. Then the reactor is closed again and the unit begins operation by activation of the main switch. Simultaneously, both cooling cycles are activated and the pressure container wall is heated to 100° C. Then a porcelain boat with a weighed-in amount of monomer is placed in the sublimation zone and the latter is closed again. The reactor is then evacuated to a base pressure of 0.03 mbar. Now a carrier gas stream of 20 sccm is started and then a working pressure of 0.2 mbar is established. Now a constant carrier gas flow and working pressure are awaited. Now the desired pyrolysis temperature of 680° C. is set and one waits until this temperature is reached in the pyrolysis zone. Then the sample container is made. to rotate with a rotation speed of 20 revolutions/min and the sublimation zone is heated to 290° C. The coating process is verified with the help of the layer thickness monitor. When the desired layer thickness of 280 nm is reached, the coating process can be ended. For this purpose the furnace controller, the torque motor of the sample container and the carrier gas stream are shut off, the flow control valve is opened and evacuated again to base pressure. Then the pump is turned off, the unit is ventilated with the ventilator valve, and the sample is removed.

To couple DTPA by a spacer molecule, the coated stent is incubated in 500 ml of a 10% by weight ethereal hexamethylenediisocyanate solution for 12 hours at room temperature. Then the sample is washed with ether and dried in a vacuum. Then the stent coated this way is incubated with a solution of DTPA anhydride in DMSO for 2 hours at 40° C. After cleaning it again, the surface is charged in the usual way with $^{188}$Re ions.

What is claimed is:

1. A polymer-coated stent, comprising a base stent on which a polymer is applied that has a hydrophilic chelating or inclusion agent covalently bonded to the surface thereof, and has one or more radioisotopes and/or one or more therapeutic agents either complexed with the hydrophilic chelating or inclusion agent or forms an inclusion compound with the hydrophilic chelating or inclusion agent on the surface of the stent.

2. A polymer-coated stent according to claim 1, wherein the hydrophilic chelating or inclusion agent is DTPA, DOTA, DO3A, or TTHA or a derivative thereof.

3. A polymer-coated stent according to claim 1, wherein the hydrophilic chelating or inclusion agent is BOPTA, butylphenyl-DTPA, DTPA-BMEA, DTPA-BMA, dicyclohexyl-DTPA, dicyclohexyl-DOTA, DPDP, a perhydrin derivative, a DTPA- or DOTA-substituted polymer, GlyMeDOTA or a GlyMeDOTA-substituted polymer.

4. A polymer-coated stent according to claim 1, wherein the one or more radioisotopes are selected from the group consisting of radioisotopes of the elements Ag, Au, Ba, Bi, Co, Cr, Cu, Fe, Ga, Gd, Hg, Ho, In, Ir, Lu, Mn, Pb, Pd, Pm, Re, Rh, Ru, Sb, Sc, Sm, Tb, Tc, Mo and Y.

5. A polymer-coated stent according to claim 4, wherein the one or more radioisotopes are selected from the group consisting of $^{186}$Re, $^{188}$Re, $^{111}$In, $^{90}$Y, $^{55}$Co, $^{57}$Co, $^{55}$Fe and $^{99}$Mo.

6. A polymer coated stent of claim 4, wherein the radioisotopes are permanently bonded to the polymer surface.

7. A polymer coated stent of claim 4, wherein the radioisotopes are $^{55}$Co and $^{55}$Fe or $^{99}$Mo and $^{57}$Co.

8. A polymer-coated stent according to claim 1, wherein the base stent is a nitinol stent.

9. A polymer-coated stent according to claim 1, wherein the hydrophilic chelating or inclusion agent is a cyclodextrin.

10. A polymer-coated stent according to claim 9, wherein the one or more therapeutic agents is a prostaglandin derivative.

11. A polymer-coated stent according to claim 1, wherein one or more radioisotopes are complexed with the hydrophilic chelating or inclusion agent or form an inclusion compound with the hydrophilic chelating or inclusion agent on the surface of the stent.

12. A polymer-coated stent according to claim 11, wherein the therapeutic agent is iloprost.

13. A polymer-coated stent according to claim 1, wherein the one or more therapeutic agents is a prostaglandin derivative.

14. A method for treating or preventing stenoses, comprising implanting a stent according to claim 1 into a blood vessel.

15. A polymer-coated stent according to claim 1, wherein the hydrophilic chelating or inclusion agent is a complexing agent.

16. In a method of implanting a stent into a patient, wherein the stent is a polymer-coated stent according to claim 1.

17. A kit comprising a polymer-coated stent according to claim 1 and one or more solutions, each solution comprising one or more radioactive isotopes and/or one or more therapeutic agents.

18. A method of preparing a stent by using a kit according to claim 17, comprising dipping the polymer-coated stent into the one or more solutions.

19. A method of preparing a polymer-coated stent according to claim 1, comprising dipping an uncoated stent into one or more solutions, each solution comprising one or more polymers, one or more radioactive isotopes, one or more therapeutic agents, and one or more hydrophilic chelating or inclusion agents.

20. A method according to claim 19, wherein the hydrophilic chelating or inclusion agent is cyclodextrin.

21. A polymer-coated stent according to claim 1, wherein the hydrophilic chelating or inclusion agent is a therapeutic agent, or wherein the hydrophilic chelating or inclusion agent has an affinity for a therapeutic agent.

22. A polymer-coated stent according to claim 21, wherein the hydrophilic chelating or inclusion agent that has as affinity for a therapeutic agent forms a complex with a therapeutic agent, or forms an inclusion compound with a therapeutic agent, in a manner that the complex or inclusion compound are carried on the surface of the polymer.

23. A polymer coated stent according to claim 1, wherein the polymer is polyurethane, polylactic acid, polyglycolic acid or copolymers thereof.

24. A polymer coated stent according to claim 1, wherein the polymer is a polyethylene glycol, a polysaccharide, a cyclodextrin or a polyaminopolycarboxylic acid.

25. A polymer-coated stent according to claim 1, consisting essentially of a base stent on which a polymer is applied that has a hydrophilic chelating or inclusion agent covalently bonded to the surface thereof, and has one or more radioisotopes and/or one or more therapeutic agents either complexed with the hydrophilic chelating or inclusion agent or forms an inclusion compound with the hydrophilic chelating or inclusion agent on the surface of the stent.

26. A polymer-coated stent according to claim 1, consisting of a base stent on which a polymer is applied that has a hydrophilic chelating or inclusion agent covalently bonded to the surface thereof, and has one or more radioisotopes and/or one or more therapeutic agents either complexed with the hydrophilic chelating or inclusion agent or forms an inclusion compound with the hydrophilic chelating or inclusion agent on the surface of the stent.

27. A process for preparing a polymer-coated stent, comprising coating a metallic base stent by chemical vapor deposition with a polymer that has functional groups, and covalently bonding a hydrophilic chelating or inclusion agent by chemical reaction to the functional groups.

28. A process for preparing a polymer-coated stent, comprising coating a metallic base by chemical vapor deposition with a polymer that has functional groups, then treating the coated metallic base stent with a solution that contains spacer molecules whereby the spacer molecules covalently bond to the functional groups, and then further treating the coated metallic base stent with a solution that contains a hydrophilic chelating or inclusion agent that covalently bonds to the spacer molecules and/or the functional groups that do not contain a spacer molecule.

29. A process for preparing a polymer-coated stent, comprising coating a base stent with a polymer having functional groups by plasma polymerization, and covalently bonding a hydrophilic chelating or inclusion agent by chemical reaction to the functional groups.

30. A process for preparing a polymer-coated stent, comprising coating abase stent with a polymer having functional groups by plasma polymerization, then treating the coated base stent with a solution that contains spacer molecules whereby the spacer molecules covalently bond to the functional groups, and then further treating the base stent with a solution that contains a hydrophilic chelating or inclusion agent that covalently bonds to the spacer molecules and/or the functional groups that do not contain a spacer molecule.

31. A process for preparing a polymer-coated stent, comprising coating a metallic base stent with a polymer having functional groups by chemical vapor deposition, and covalently bonding a cyclodextrin derivative by chemical reaction to the functional groups.

32. A process for preparing a polymer-coated stent, comprising coating a metallic base stent with a polymer having functional groups by chemical vapor deposition, then treating the coated metallic base stent with a solution containing spacer molecules whereby the spacer molecules covalently bond to the functional groups, and then further treating the base stent with a solution containing a cyclodextrin derivative that covalently bonds to the spacer molecules and/or the functional groups that do not contain a spacer molecule.

33. A polymer-coated stent, comprising a base stent on which a polymer is applied that has a hydrophilic chelating or inclusion agent covalently bonded to the surface thereof, and has one or more radioisotopes and/or one or more therapeutic agents either complexed with the hydrophilic chelating or inclusion agent or forms an inclusion compound with the hydrophilic chelating or inclusion agent on the surface of the stent, wherein the polymer layer is an outermost or exterior polymer layer on the surface of the stent.

* * * * *